(12) United States Patent
Uchiyama

(10) Patent No.: US 10,327,692 B2
(45) Date of Patent: Jun. 25, 2019

(54) APPARATUS FOR ASSESSING MUSCLE QUALITY

(71) Applicant: TANITA CORPORATION, Itabashi-ku, Tokyo (JP)

(72) Inventor: Tomoka Uchiyama, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 75 days.

(21) Appl. No.: 14/452,144

(22) Filed: Aug. 5, 2014

(65) Prior Publication Data

US 2015/0045690 A1     Feb. 12, 2015

(30) Foreign Application Priority Data

Aug. 6, 2013  (JP) .................................. 2013-163362

(51) Int. Cl.
*A61B 5/00*     (2006.01)
*A61B 5/053*    (2006.01)

(52) U.S. Cl.
CPC .......... *A61B 5/4519* (2013.01); *A61B 5/0537* (2013.01); *A61B 5/7278* (2013.01); *A61B 5/742* (2013.01)

(58) Field of Classification Search
CPC ..... A61B 5/4519; A61B 5/742; A61B 5/0537; A61B 5/7278
See application file for complete search history.

(56) References Cited

U.S. PATENT DOCUMENTS

2011/0251513 A1*  10/2011  Chetham .............. A61B 5/0537
                                               600/547
2013/0172775 A1    7/2013  Ozawa

FOREIGN PATENT DOCUMENTS

JP    2004-255120 A    9/2004
JP    2012-210355 A    11/2012

OTHER PUBLICATIONS

"Circuitry" The American Heritage Dictionary of the English Language, Fifth Edition (2014), Houghton Mifflin Harcourt Publishing Company. Retrieved from <https://ahdictionary.com/word/search.html?q=circuitry> on Jun. 13, 2015.*

(Continued)

*Primary Examiner* — David J. McCrosky
(74) *Attorney, Agent, or Firm* — Sughrue Mion, PLLC

(57) ABSTRACT

An apparatus for assessing muscle quality includes a first acquisition unit that acquires bioelectric information including at least one of (i) a resistance component and a reactance component of bioelectrical impedance and (ii) first impedance measured by supplying alternating current at a predetermined low frequency to a living organism and second impedance measured by supplying alternating current at a predetermined high frequency to the living organism; a second acquisition unit that acquires a physical parameter related to physique of the living organism; and a calculation unit that calculates an index in accordance with a proportion, in muscle tissue, of muscle fiber to interstitial tissue based on the physical parameter and on at least one of a first parameter represented as a ratio between the resistance component and the reactance component and a second parameter represented as a ratio between the first impedance and the second impedance.

20 Claims, 9 Drawing Sheets

(56) References Cited

OTHER PUBLICATIONS

Khalil, et al. "The theory and fundamentals of bioimpedance analysis in clinical status monitoring and diagnosis of diseases." Sensors 14.6 (2014): 10895-10928.*

Internet Archive, Tanita website, "BC-1000plus Ant+ Radio Wireless Body Composition Monitor" 2013.*

Communication dated Jan. 20, 2015, issued by the European Patent Office in corresponding Application No. 14180038.3.

Marini, Elisabetta et al., "The potential of classic and specific bioelectrical impedance vector analysis for the assessment of sarcopenia and sarcopenic obesity", Clinical Interventions in Aging 2012, vol. 7, 2012, pp. 585-590, XP002734149.

Sammarco R et al., "Screening for Sarcopenia in Obesity", Journal of Physics: Conference Series, Institute of Physics Publishing, Bristol, GB, vol. 434, No. 1, Apr. 18, 2013, 12044, pp. 1-4 XP020240783.

Communication from the European Patent Office dated Apr. 25, 2016 in counterpart application No. 14180038.3.

Communication dated Feb. 7, 2017, issued form the Japan Patent Office in the corresponding Japanese Patent Application No. 2013-163362.

Marini, Elisabetta et al., "The potential of classic and specific bioelectrical impedance vector analysis for the assessment of sarcopenia and sarcopenic obesity", Clinical Interventions in Aging 2012, vol. 7, 2012, pp. 585-591, XP002734149.

Kern, Philip et al. "Effect of Weight Loss on Muscle Fiber Type, Fiber Size, Capillarity, and Succinate Dehydrogenase Activity in Humans", The Journal of Clinical Endocrinology & Metabolism, 1999, vol. 84, No. 11, pp. 4185-4190.

Communication dated Sep. 30, 2017, from State Intellectual Property Office of the P.R.C. in counterpart application No. 201410385047.4.

* cited by examiner

Volume V = cross-sectional area A × length L

APPARATUS FOR ASSESSING MUSCLE QUALITY

CROSS REFERENCE TO RELATED APPLICATION

This application claims priority to and the benefit of Japanese Patent Application No. 2013-163362 filed Aug. 6, 2013, the entire contents of which are incorporated herein by reference.

TECHNICAL FIELD

The present invention relates to an apparatus for assessing muscle quality and in particular to an apparatus for assessing muscle quality that can calculate an index in accordance with the proportion of muscle fiber in muscle tissue.

BACKGROUND ART

A known body composition meter using bioelectrical impedance analysis calculates an index related to body fat or muscle mass based on impedance that is measured by contacting impedance measurement electrodes to a hand or leg, applying current, and measuring the voltage.

JP2012-210355A discloses a method for assessing muscle mass that judges the degree of muscular development (muscle cells becoming thicker) and muscular atrophy (muscle cells becoming thinner) based on the ratio of impedance measured by applying alternating current at a predetermined high frequency to impedance measurement electrodes to impedance measured by applying alternating current at a predetermined low frequency to impedance measurement electrodes.

JP2012-210355A discloses judging the degree of muscular development and muscular atrophy by assessing the ratio between intracellular fluid and extracellular fluid (referred to below as "intra/extracellular fluid ratio").

SUMMARY OF INVENTION

However, when intracellular fluid and extracellular fluid decrease by the same degree, for example due to advancing age, the intra/extracellular fluid ratio does not change greatly. Therefore, even if muscle cells undergo muscular atrophy, it is difficult to judge such muscular atrophy.

When intracellular fluid and extracellular fluid increase by the same degree, for example during a growing phase, the intra/extracellular fluid ratio similarly does not change greatly. Therefore, even if muscle cells undergo muscular development, it is difficult to judge such muscular development.

The present invention has been conceived in light of the above circumstances, and it is an object thereof to provide an apparatus for assessing muscle quality that can calculate an index reflecting atrophy or development of muscle cells (i.e. muscle fiber) even when intracellular fluid and extracellular fluid decrease or increase by the same degree.

To achieve the above object, an apparatus for assessing muscle quality according to an aspect of the present invention comprises a first acquisition unit configured to acquire bioelectric information including at least one of (i) a resistance component and a reactance component of bioelectrical impedance and (ii) first impedance measured by supplying alternating current at a predetermined low frequency to a living organism and second impedance measured by supplying alternating current at a predetermined high frequency to the living organism; a second acquisition unit configured to acquire a physical parameter related to physique of the living organism; and a calculation unit configured to calculate an index in accordance with a proportion, in muscle tissue, of muscle fiber to interstitial tissue based on the physical parameter and on at least one of a first parameter represented as a ratio between the resistance component and the reactance component and a second parameter represented as a ratio between the first impedance and the second impedance.

In the above aspect of the present invention, the physical parameter may include a parameter related to muscle mass of the living organism.

In the above aspect of the present invention, the physical parameter may include a parameter related to weight of the living organism.

In the above aspect of the present invention, the physical parameter may include an impedance index of the living organism.

In the above aspect of the present invention, in addition to calculating the index in accordance with the proportion, in muscle tissue, of muscle fiber to interstitial tissue, the calculation unit may use the same parameters as the parameters used to calculate the index and uses a different contributing ratio for at least one of the parameters than when calculating the index in order to calculate a muscle mass index.

The apparatus for assessing muscle quality according to the above aspect of the present invention may further comprise a display unit configured to display a calculated value of the index in accordance with the proportion, in muscle tissue, of muscle fiber to interstitial tissue and a calculated value of the muscle mass index, or information based on a calculated value of the index in accordance with the proportion, in muscle tissue, of muscle fiber to interstitial tissue and on a calculated value of the muscle mass index.

The apparatus for assessing muscle quality according to the above aspect of the present invention may further comprise an interface for exchanging information with an external device.

In the above aspect of the present invention, the first acquisition unit may receive at least one of the first parameter and the second parameter from the external device via the interface, and the second acquisition unit may receive the physical parameter from the external device via the interface.

In the above aspect of the present invention, the calculation unit may transmit the calculated index to the external device via the interface.

In addition to at least one of the first parameter represented as the ratio between the resistance component R and the reactance component X of bioelectrical impedance and the second parameter represented as the ratio between the first impedance $Z_{low}$ and the second impedance $Z_{high}$, the apparatus for assessing muscle quality according to the above aspect of the present invention takes into consideration a physical parameter that is a parameter related to the physique of the living organism and calculates an index in accordance with the proportion, in muscle tissue, of muscle fiber to interstitial tissue. Therefore, an index reflecting the magnitude of muscle fiber can be calculated even when intracellular fluid and extracellular fluid decrease or increase by the same degree.

By the physical parameter including at least one of a parameter related to muscle mass, a parameter related to weight, and the impedance index of the living organism, the accuracy of the above-described index that reflects the difference in magnitude of the muscle fiber can be improved. In particular, when at least the parameter related to muscle mass is included, the accuracy of the above-described index can be improved even further.

By the calculation unit calculating the index in accordance with the proportion, in muscle tissue, of muscle fiber to interstitial tissue and calculating the muscle mass index, muscle strength can be assessed comprehensively based on muscle mass and quality. Therefore, as compared to when assessment is based on one of these factors, muscle strength can be assessed more accurately. Accordingly, by displaying on a display unit the calculated value of the indices of muscle mass and quality, or information based on these calculated values, users can more accurately grasp the state of their own muscles.

According to the present invention, an index reflecting atrophy or development of muscle fiber can be calculated even when intracellular fluid and extracellular fluid decrease or increase by the same degree.

BRIEF DESCRIPTION OF DRAWINGS

The present invention will be further described below with reference to the accompanying drawings, wherein.

DESCRIPTION OF EMBODIMENTS

With reference to FIGS. 1 to 8, the following describes an embodiment of an apparatus for assessing muscle quality according to the present invention. The same components are labeled with the same reference signs in each figure.

Figure 1:
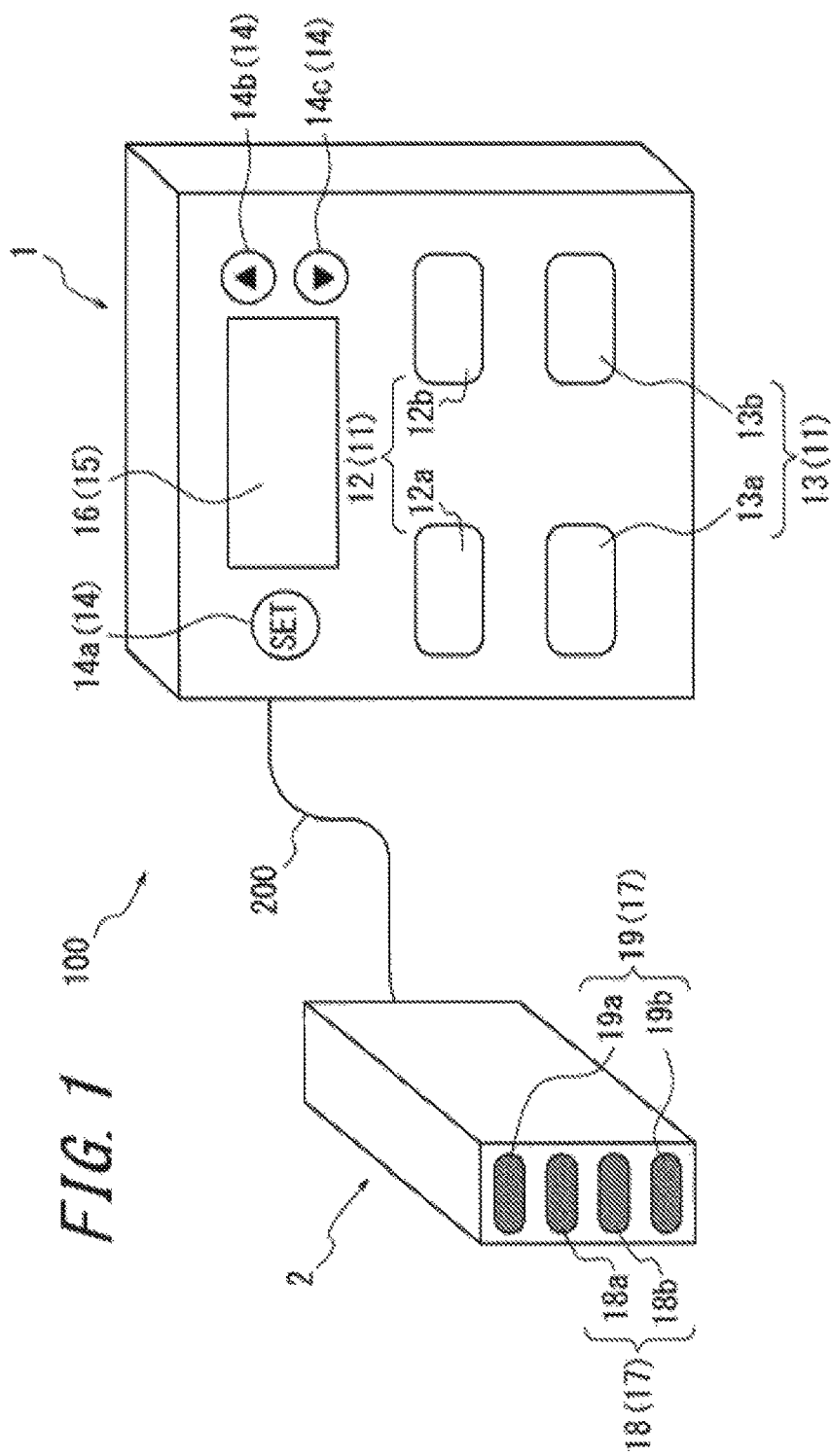
FIG. 1 is a perspective view illustrating an apparatus 100 for assessing muscle quality as an embodiment of the present invention.

First, an embodiment of an apparatus for assessing muscle quality according to the present invention is described. FIG. 1 is a perspective view illustrating an apparatus 100 for assessing muscle quality in the present embodiment. The apparatus 100 for assessing muscle quality in the present embodiment is a body composition meter 100a, yet the present invention is not limited in this way.

As illustrated in FIG. 1, the apparatus 100 for assessing muscle quality in the present embodiment includes a platform unit 1 on which the subject being measured stands and a grip unit 2 that the subject being measured grips with both hands. The platform unit 1 and the grip unit 2 are connected by a cable 200.

<Platform Unit 1>

The platform unit 1 includes a first electrode unit 11 provided on the surface on which the subject being measured stands with both feet, a physical information input unit 14 that allows for input of information related to the body and forms a portion of the below-described second acquisition unit 21 (see FIG. 2), and a display unit 16 that displays information related to the body which is input from the physical information input unit 14, for example, and is part of an output unit 15 (see FIG. 2). The first electrode unit 11 forms part of the below-described first acquisition unit 20 (see FIG. 2) and includes a pair of first current supply electrodes 12 (represented as electrodes 12a and 12b) and a pair of first voltage measurement electrodes 13 (represented as electrodes 13a and 13b).

The pair of first current supply electrodes 12 can cause a weak alternating current to flow in the subject being measured, which is a living organism, by supplying alternating current while in contact with the bottoms of the feet of the subject being measured. Details are provided below.

The pair of first voltage measurement electrodes 13 is used to measure voltage when alternating current is supplied to the subject being measured. Details are provided below.

The physical information input unit 14 includes a setting key 14a, an up key 14b, and a down key 14c. The up key 14b and the down key 14c select information or change numerical values, and the setting key 14a sets the selected information or the numerical value. In the present embodiment, information related to the body such as the gender, age, height, and the like of the subject being measured can be input by operating the setting key 14a, up key 14b, and down key 14c.

The display unit 16 changes the displayed information in response to operation of the physical information input unit 14 by the subject being measured. While viewing the display on the display unit 16, the subject being measured can input information related to the body. The display unit 16 can display the results of measurement by the apparatus 100 for assessing muscle quality, and the subject being measured can see the results via the display on the display unit 16.

<Grip Unit 2>

The grip unit 2 includes a pair of second current supply electrodes 18 (represented as electrodes 18a and 18b) and a pair of second voltage measurement electrodes 19 (represented as electrodes 19a and 19b) as a second electrode unit 17. Like the above-described first electrode unit 11, the second electrode unit 17 also forms part of the below-described first acquisition unit 20 (see FIG. 2). The subject being measured grips the grip unit 2 so as to contact the pair of second current supply electrodes 18. In this state, a weak alternating current is supplied to the subject being measured through the second current supply electrodes 18. The pair of second voltage measurement electrodes 19 is used to measure voltage when alternating current is supplied to the subject being measured. Note that in the present embodiment, the pair of second current supply electrodes 18 is positioned between the pair of second voltage measurement electrodes 19, yet the present invention is not limited to this arrangement. The pair of second voltage measurement electrodes 19 may be positioned between the pair of second current supply electrodes 18. Details on the second electrode unit 17 are provided below.

Figure 2:
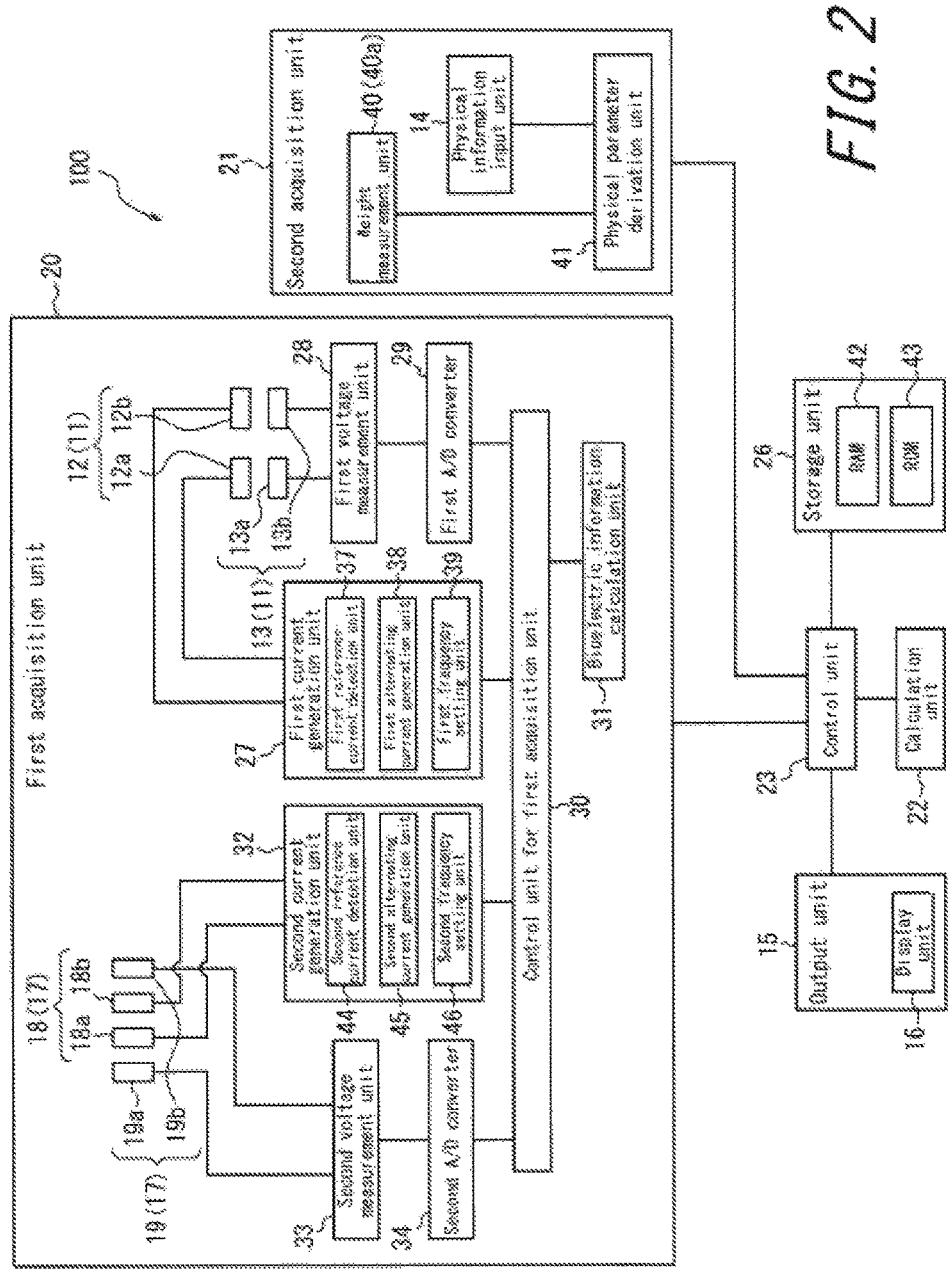
FIG. 2 is a block diagram illustrating the configuration of the apparatus 100 for assessing muscle quality.

FIG. 2 is a block diagram illustrating the configuration of the apparatus 100 for assessing muscle quality in the present embodiment. The following describes the configuration of the apparatus 100 for assessing muscle quality in detail.

As illustrated in FIG. 2, the apparatus 100 for assessing muscle quality includes the first acquisition unit 20, the second acquisition unit 21, a calculation unit 22, a control unit 23, the output unit 15, and a storage unit 26. As illustrated in FIG. 1, in the present embodiment, the second electrode unit 17 in the first acquisition unit 20 is provided in the grip unit 2, and the rest of the structure is all provided in the platform unit 1.

<First Acquisition Unit 20>

The first acquisition unit 20 can acquire bioelectric information including at least one of (i) a resistance component R and a reactance component X of bioelectrical impedance and (ii) first impedance $Z_{low}$ measured by supplying alternating current at a predetermined low frequency to the living organism and second impedance $Z_{high}$ measured by supplying alternating current at a predetermined high frequency to the living organism.

Figure 3:
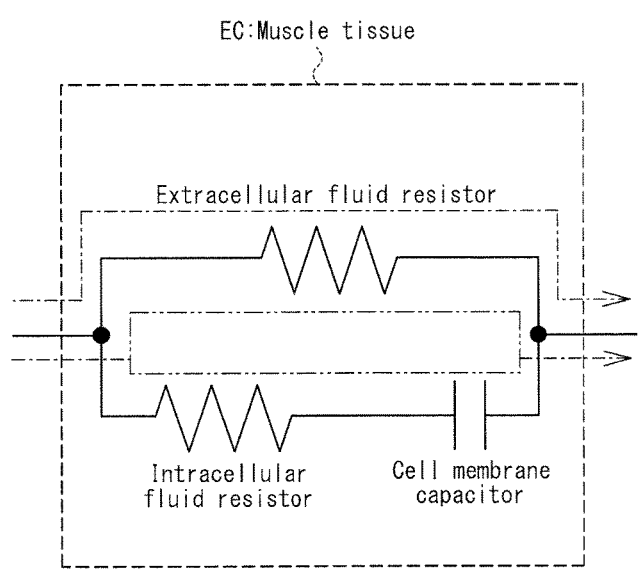
FIG. 3 is a model diagram illustrating a model of a current path in a living organism using an electrical equivalent circuit.
Figure 4:
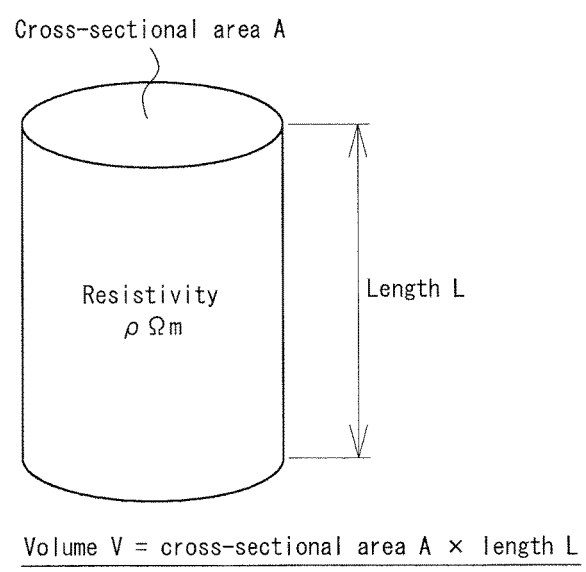
FIG. 4 is a model illustrating the relationship between volume and impedance.
Figure 5:
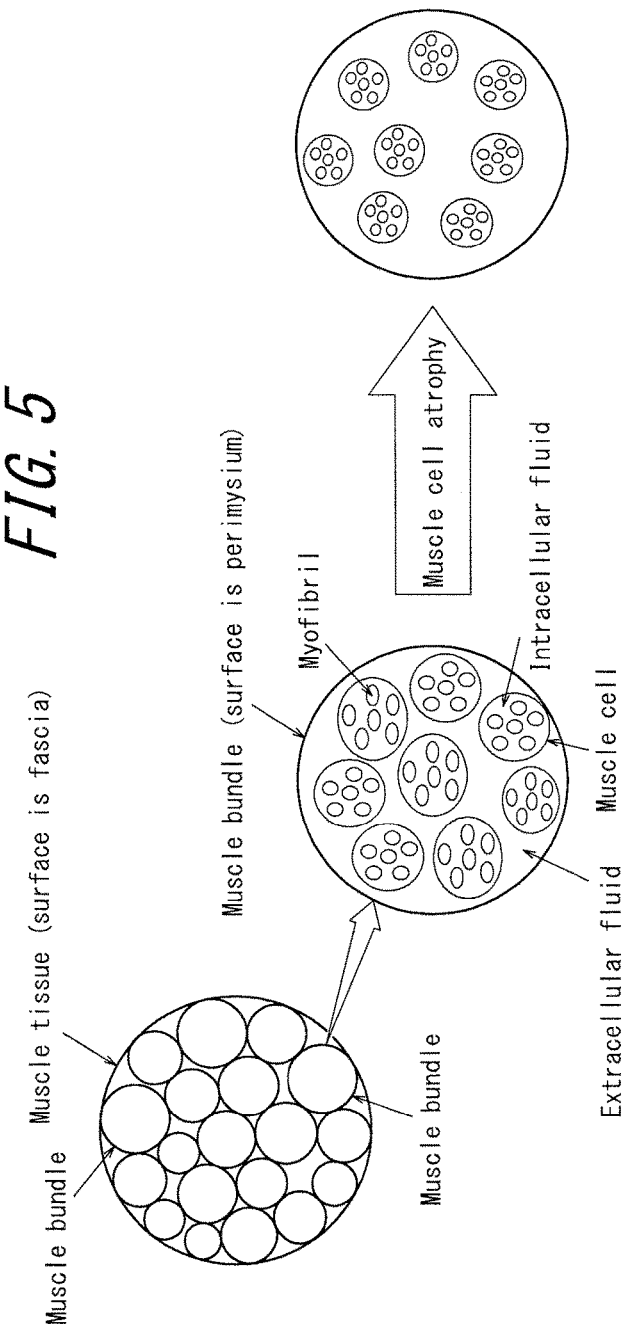
FIG. 5 is a cross-sectional model of muscle tissue illustrating a decrease in the amount of muscle intracellular fluid in muscle tissue when muscular atrophy occurs.

Here, a first parameter represented as a ratio between the resistance component R and the reactance component X of the bioelectrical impedance and a second parameter represented as a ratio between the first impedance $Z_{low}$ and the second impedance $Z_{high}$ are parameters that highly correlate with the intra/extracellular fluid ratio. The reason why is described simply with reference to FIGS. 3 to 5. FIG. 3 is a model diagram illustrating a model of a current path in a living organism using an electrical equivalent circuit, and FIG. 4 is a model illustrating the relationship between volume and impedance. FIG. 5 is a cross-sectional model of muscle tissue illustrating a decrease in the amount of muscle intracellular fluid in muscle tissue when muscular atrophy occurs.

Among body tissue, the majority of lean tissue is body water that includes many electrolytes, and electrical current flows through lean tissue easily. Fatty tissue and bone, however, is thought to be non-electrolyte tissue that includes nearly no electrolytes. Accordingly, among lean tissue, muscle tissue is electrolyte tissue, whereas bones and fatty tissue such as subcutaneous fat and visceral fat can be considered non-electrolyte tissue.

Therefore, as illustrated in FIG. 3, muscle tissue can be modeled as a circuit EC. The circuit EC illustrates the electrical equivalent circuit of the above-described electrolyte tissue and is represented by a parallel circuit between an extracellular fluid resistor and a series portion composed of an intracellular fluid resistor and a cell membrane capacitor.

The circuit EC is a model of the muscle tissue that is electrolyte tissue using a cell level. The muscle tissue includes muscle cells (muscle fiber), in which intracellular fluid is covered by a cell membrane, and extracellular fluid on the outside of the cell membranes. The intracellular fluid and the extracellular fluid function as resistors. The cell membrane is capacitive since it is formed by a lipid bilayer, and thus electrically becomes an insulator in the case of low frequency current close to direct current, so that current does not flow to the intracellular fluid. Upon increasing the frequency, however, current flows through the cell membrane and also through the intracellular fluid. Accordingly, the above-described electrical equivalent circuit can be represented with the cell membrane as a capacitor and the intracellular fluid and extracellular fluid as resistors.

In the model illustrated in FIG. 3, when using direct current, the current takes the extracellular fluid resistor as the current path, as indicated by the alternate long and short dash line. Hence, information on the extracellular fluid is also reflected in the measured value. When using alternating current, however, the current takes the extracellular fluid resistor, the intracellular fluid resistor, and the cell membrane capacitor as the current path, as indicated by the alternate long and two short dashes line. Hence, information on the extracellular fluid and the intracellular fluid is also reflected in the measured value. As the frequency increases, the effect of the cell membrane capacitor reduces, and thus the information on the intracellular fluid resistor is more greatly reflected. Accordingly, as the frequency of the current is raised, the muscle cells are reflected in the calculated impedance to a greater degree.

Taking into consideration the material model illustrated in FIG. 4, where V is volume, ρ is resistivity in Ωm, A is cross-sectional area, and L is length, the impedance Z is defined as impedance Z=ρ×L/A. Accordingly, the volume V is expressed as A×L, and volume V=A'L=ρ×L$^2$/Z. As described above, when alternating current is supplied to the living organism, in the low frequency region, current does not flow to the capacitor due to the cell membrane formed by a lipid bilayer, and almost all of the current supplied to the living organism flows through the extracellular fluid. In other words, when the bioelectrical impedance measured at a low frequency is substituted into the above equation for volume, the resulting volume can be considered to be the volume of the extracellular fluid. On the other hand, in the high frequency region, the reactance component due to the cell membrane can be ignored. Accordingly, when the bioelectrical impedance measured at a high frequency is substituted into the above equation for volume, the resulting value can be considered the volume of the entire tissue including the intracellular fluid.

During the phenomenon known as muscular atrophy, in which muscle cells become thinner, the amount of muscle intracellular fluid in muscle tissue decreases, and the amount of extracellular fluid increases, as is clear from the cross-sectional model of muscle tissue illustrated in FIG. 5. In other words, the ratio of the volume of muscle cells in the entire tissue reduces. Expressing this relationship as an equation for volume yields Equation 1 below.

$$Z_{high\_frequency}/Z_{low\_frequency} = (\rho_{high\_frequency} \times L^2/V_{high\_frequency})/(\rho_{low\_frequency} \times L^2/V_{low\_frequency}) = (\rho_{high\_frequency} \times V_{low\_frequency})/(\rho_{low\_frequency} \times V_{high\_frequency})$$

(Equation 1)

Accordingly, as described above, in the high frequency region the impedance becomes the impedance for the entire tissue, and in the low frequency region, the impedance becomes the impedance for the extracellular fluid. Therefore, if the resistivity for a low frequency and the resistivity for a high frequency are nearly equal, the above equation can be expressed as Equation 2 below.

$$Z_{high\_frequency}/Z_{low\_frequency} \approx (\rho_{entire\_tissue} \times V_{extracellular\_fluid})/(\rho_{extracellular\_fluid} \times V_{entire\_tissue}) \approx V_{extracellular\_fluid}/V_{entire\_tissue}$$

(Equation 2)

where $(0 < Z_{high\_frequency}/Z_{low\_frequency} < 1)$

In other words, it is clear that the ratio between the bioelectrical impedances measured at a low frequency and at a high frequency becomes the ratio of the amount of extracellular fluid in the target tissue. As muscular atrophy continues, the amount of extracellular fluid increases, as described above. Accordingly, the impedance ratio expressed by the equation above is thought to approach 1.

It is thus clear that the second parameter is a parameter that highly correlates with the intra/extracellular fluid ratio. Like the second parameter, the first parameter, which is represented as a ratio between the resistance component R and the reactance component X of the bioelectrical impedance, is also a parameter that highly correlates with the intra/extracellular fluid ratio. When cells atrophy, the proportion of extracellular fluid in the muscle tissue rises, and the resistance component R increases. Conversely, because the cells atrophy and shrink, or because atrophy progresses and a portion of the cells is eliminated, reducing the number of cells, the effect of the capacitance component of the cell membranes reduces, causing the reactance component X to reduce. In other words, it is clear that the first parameter represented as a ratio between the resistance component R and the reactance component X of the bioelectrical impedance is a parameter that changes along with a change in the size of the muscle cells and has a high correlation with the intra/extracellular fluid ratio.

As illustrated in FIG. 2, the first acquisition unit 20 in the present embodiment includes a first current generation unit 27, the first electrode unit 11, a first voltage measurement unit 28, a first analog/digital converter 29 (referred to below as the "first A/D converter 29"), a second current generation unit 32, the second electrode unit 17, a second voltage measurement unit 33, a second analog/digital converter 34 (referred to below as the "second A/D converter 34"), a control unit 30 for the first acquisition unit, and a bioelectric information calculation unit 31 for the first acquisition unit. The second electrode unit 17 is provided in the grip unit 2, whereas the other components are provided in the platform unit 1.

The first current generation unit 27 outputs alternating current that flows between the pair of first current supply electrodes 12 (12a and 12b). Specifically, the first current generation unit 27 includes a first reference current detection unit 37, a first alternating current generation unit 38, and a first frequency setting unit 39. The first frequency setting unit 39 is controlled by the control unit 30 for the first acquisition unit and sets a predetermined frequency. The first reference current detection unit 37 detects current flowing in the subject being measured as a reference current and outputs the detected current as a reference current detection signal to the first alternating current generation unit 38. The first alternating current generation unit 38 generates alternating current having a value based on the reference current detection signal and the frequency set by the first frequency setting unit 39. This alternating current is supplied to the living organism via the pair of first current supply electrodes 12.

The first current supply electrodes 12a and 12b forming the pair of first current supply electrodes 12 are exposed on the platform unit 1, as illustrated in FIG. 1, and the subject being measured stands on the platform unit 1 so that the backs of the feet respectively contact the first current supply electrodes 12a and 12b. In this state, current flows to the subject being measured, which is a living organism, by the alternating current being supplied to the subject being measured via the pair of first current supply electrodes 12.

Like the first current supply electrodes 12a and 12b, the first voltage measurement electrodes 13a and 13b forming the pair of first voltage measurement electrodes 13 are exposed on the platform unit 1. The subject being measured stands on the platform unit 1 so that the backs of the feet respectively contact the first voltage measurement electrodes 13a and 13b. In other words, the subject being measured stands on the platform unit 1 so that the back of one foot contacts the first current supply electrode 12a and the first voltage measurement electrode 13a, and the back of the other foot contacts the first current supply electrode 12b and the first voltage measurement electrode 13b. Accordingly, the pair of first voltage measurement electrodes 13 allow for measurement of the voltage drop between the feet when alternating current is supplied to the living organism through the pair of first current supply electrodes 12.

The first voltage measurement unit 28 measures the voltage between the first voltage measurement electrodes 13a and 13b. The analog potential difference signal measured by the first voltage measurement unit 28 is converted to a digital signal by the first analog/digital converter 29 and input into the control unit 30 for the first acquisition unit.

Using the voltage measured by the first voltage measurement unit 28 and the reference current detected by the first reference current detection unit 37 as the current supplied to the living organism through the pair of first current supply electrodes 12, the bioelectric information calculation unit 31 for the first acquisition unit acquires bioelectric information including at least one of (i) the resistance component R and the reactance component X, and (ii) the first impedance $Z_{low}$ and the second impedance $Z_{high}$.

The second current generation unit 32 in the first acquisition unit 20 includes a second reference current detection unit 44, a second alternating current generation unit 45, and a second frequency setting unit 46. The second current generation unit 32, second voltage measurement unit 33, second A/D converter 34, second electrode unit 17, control unit 30 for the first acquisition unit, and bioelectric information calculation unit 31 for the first acquisition unit acquire bioelectric information by the same method as the above-described method for acquiring bioelectric information via the first electrode unit 11. The subject being measured grips the grip unit 2 so that one hand contacts the second current supply electrode 18a and the second voltage measurement electrode 19a and the other hand contacts the second current supply electrode 18b and the second voltage measurement electrode 19b, and in this state, bioelectric information is acquired by supplying alternating current to the subject being measured. In the present embodiment, the first acquisition unit 20 includes the control unit 30 for the first acquisition unit as a control unit, yet a first control unit for the first electrode unit 11 and a second control unit for the second electrode unit 17 may be provided. Furthermore, in the present embodiment, the bioelectric information calculation unit 31 for the first acquisition unit is provided as the bioelectric information calculation unit, yet a first bioelectric information calculation unit for the first electrode unit 11 and a second bioelectric information calculation unit for the second electrode unit 17 may be provided. The control unit 23 in the apparatus 100 for assessing muscle quality may also be configured to include the function of the control unit 30 for the first acquisition unit.

In the present embodiment, bioelectric information is acquired by the first electrode unit 11 and the second electrode unit 17 separately supplying current and measuring voltage, yet acquisition of bioelectric information is not limited to this method. Specifically, the first acquisition unit 20 includes the first electrode unit 11 and the second electrode unit 17, and therefore includes a total of four current supply electrodes 12a, 12b, 18a, and 18b and a total of four voltage measurement electrodes 13a, 13b, 19a, and 19b. It is thus possible to achieve a structure that can cause alternating current to flow between any two current supply electrodes and a structure that can measure voltage between any two voltage measurement electrodes. With this structure, the first acquisition unit 20 can acquire bioelectric information for various body parts of the living organism (the limbs and torso, i.e. five body parts).

<Method for the First Acquisition Unit 20 to Acquire the Resistance Component R and the Reactance Component X>

The method for the first acquisition unit 20 to acquire the resistance component R and the reactance component X of the bioelectrical impedance is now described.

Once voltage measurement by the first voltage measurement unit 28 is complete when supplying the living organism with alternating current at a predetermined frequency (for example, 50 kHz) through the pair of first current supply electrodes 12, the voltage measured by the first voltage measurement unit 28 and the reference current detected by the first reference current detection unit 37 as the current applied to the pair of first current supply electrodes 12 are used to perform waveform processing such as a Discrete Fourier Transform (DFT). In this way, the bioelectric information calculation unit 31 for the first acquisition unit can calculate the resistance component R and the reactance component X. Furthermore, in the present embodiment, the bioelectric information calculation unit 31 for the first acquisition unit can calculate the first parameter represented as the ratio between the resistance component R and the reactance component X from the resistance component R and the reactance component X calculated by the bioelectric information calculation unit 31 for the first acquisition unit. Note that the case of using alternating current at a frequency of 50 kHz is described in the present embodiment, yet the present invention is not limited in this way. As the frequency range reflecting cell characteristics, any frequency in the range of 1 kHz to 10 MHz may be used.

Furthermore, in the present embodiment, the first parameter is calculated using the resistance component R and the reactance component X obtained with the first electrode unit 11, yet the resistance component R and the reactance component X obtained with the second electrode unit 17 may be used to calculate the first parameter. The resistance component R and the reactance component X of the bioelectrical impedance obtained using both the electrodes of the first electrode unit 11 and the electrodes of the second electrode unit 17 may also be used to calculate the first parameter. Note that it suffices for the first parameter to be represented as the ratio of the resistance component R and the reactance component X, and the first parameter may be either resistance component R/reactance component X or reactance component X/resistance component R.

<Method for the First Acquisition Unit 20 to Acquire the First Impedance $Z_{low}$ and the Second Impedance $Z_{high}$>

The following describes the method for the first acquisition unit 20 to acquire the first impedance $Z_{low}$ measured by supplying alternating current at a predetermined low frequency to the living organism and the second impedance $Z_{high}$ measured by supplying alternating current at a predetermined high frequency to the living organism.

By the same method as described above, the bioelectric information calculation unit 31 for the first acquisition unit calculates a resistance component $R_{low}$ and reactance component $X_{low}$ when supplying the subject being measured with alternating current at a predetermined low frequency (for example, 5 kHz) through the pair of first current supply electrodes 12 and calculates a resistance component $R_{high}$ and reactance component $X_{high}$ when supplying the subject being measured with alternating current at a predetermined high frequency (for example, 250 kHz) through the pair of first current supply electrodes 12. Since the impedance Z can be calculated as $Z=(R^2+X^2)^{1/2}$, the bioelectric information calculation unit 31 for the first acquisition unit can use this equation to calculate the first impedance $Z_{low}$ and the second impedance $Z_{high}$. Furthermore, in the present embodiment, the bioelectric information calculation unit 31 for the first acquisition unit can calculate the second parameter represented as the ratio between the first impedance $Z_{low}$ and the second impedance $Z_{high}$ from the first impedance $Z_{low}$ and the second impedance $Z_{high}$ calculated by the bioelectric information calculation unit 31 for the first acquisition unit. Note that in the present embodiment, an example of the predetermined low frequency being 5 kHz is described, yet any low frequency yielding a value near the bioelectrical impedance when applying direct current may be used. Accordingly, the predetermined low frequency may be in a frequency range of 10 kHz or less. Furthermore, in the present embodiment, an example of the predetermined high frequency being 250 kHz is described, yet any frequency yielding a value near the bioelectrical impedance when the frequency is infinite may be used. Accordingly, the predetermined high frequency may be in a frequency range of 200 kHz or more.

In the present embodiment, the second parameter is calculated using the resistance component R and the reactance component X obtained with the first electrode unit 11, yet the resistance component R and the reactance component X obtained with the second electrode unit 17 may be used to calculate the second parameter. The resistance component R and the reactance component X of the bioelectrical impedance obtained using both the electrodes of the first electrode unit 11 and the electrodes of the second electrode unit 17 may also be used to calculate the second parameter. It also suffices for the second parameter to be represented as the ratio of the first impedance $Z_{low}$ and the second impedance $Z_{high}$, and the second parameter may be either first impedance $Z_{low}$/second impedance $Z_{high}$ or second impedance $Z_{high}$/first impedance $Z_{low}$.

<Second Acquisition Unit 21>

The second acquisition unit 21 can acquire a physical parameter related to the physique of the living organism. In this context, "physique" refers to the body's build, such as being bony, muscular, fat, etc., and is an external condition indicated by bone structure, muscle mass, subcutaneous fat, weight, height, and the like. Examples of the physical parameter include a parameter related to the muscle mass of the living organism, a parameter related to the weight of the living organism, and the impedance index of the living organism.

Specifically, the parameter related to the muscle mass of the living organism may for example be the muscle mass of the entire body or a portion thereof, the proportion of total body muscle mass to body weight (referred to below as "total body muscle ratio"), the proportion of muscle mass of each body part to the weight of that body part (referred to below as "body part muscle ratio"), or the proportion of muscle mass of each body part to body weight (referred to below as "body part/body weight muscle ratio").

Examples of the parameter related to the weight of the living organism include Body Mass Index (BMI, represented as body weight/height), body weight of the living organism, the weight of each body part of the living organism, and the like. Note that "body weight of the living organism" refers to the total body weight, whereas the "weight of each body part of the living organism" refers to the sum of the masses of muscle, fat, and bone for each body part.

Furthermore, as the impedance index of the living organism, height (Ht) squared divided by the absolute value of impedance (|Z|) is used ($Ht^2/|Z|$). As the height (Ht), it is possible to use the body height, or the length of a body part, which is input from the physical information input unit 14, of the subject being measured as the living organism. When the living organism is assumed to be one homogenous cylinder, or to be the sum of five homogenous cylinders for the limbs and torso, then because the volume of the homogenous cylinder(s) is proportional to the impedance index, the impedance index of the living organism can be used as a parameter correlating with the volume of the total body or the body parts.

As the physical parameter, the muscle mass of the total body or of body parts can be estimated statistically using bioelectric characteristics. The gender, age or the like which is input from the physical information input unit 14 may also be used as the physical parameter.

As illustrated in FIG. 2, the second acquisition unit 21 in the present embodiment includes a weight measurement unit 40 that measures the weight of the living organism, the physical information input unit 14 that allows for external input of information related to the body of the living organism, and a physical parameter derivation unit 41 that can derive (i) a physical parameter related to the muscle mass of the living organism based on the value measured by the weight measurement unit 40 and on the bioelectric information acquired by the first acquisition unit 20, (ii) a physical parameter related to the weight of the living organism based on the value measured by the weight measurement unit 40 and on information related to the body which is input from the physical information input unit 14, and (iii) an impedance index as a physical parameter based on information related to the body which is input from the physical information input unit 14 and on the bioelectric information acquired by the first acquisition unit 20. Note that the weight measurement unit 40 in the present embodiment is a body weight measurement unit 40a using a load cell such as a strain gauge or the like, yet the present invention is not limited in this way.

The weight measurement unit 40 in the present embodiment can measure the body weight of the subject being measured by the subject being measured standing on the exposed face of the first electrode unit 11 in the platform unit 1.

As described above, the physical information input unit 14 can receive input of information related to the body such as the gender, age, height, and the like of the subject being measured.

The physical parameter derivation unit 41 derives a plurality of physical parameters using the value measured by the weight measurement unit 40, the information related to the body which is input from the physical information input unit 14, and the bioelectric information acquired by the first acquisition unit 20.

Specifically, the physical parameter derivation unit 41 uses the value of the body weight measured by the weight measurement unit 40 and the bioelectrical impedance acquired by the first acquisition unit 20 as bioelectric information in order to derive, by calculation, the total body muscle ratio and the body part/body weight muscle ratio as a physical parameter related to the muscle mass of the living organism. In greater detail, the total body muscle ratio and body part/body weight muscle ratio are derived using fat mass, estimated bone mass, and the like that are calculated from the measured values of the bioelectrical impedance and body weight.

The physical parameter derivation unit 41 uses the value of the body weight measured by the weight measurement unit 40 and the height which is input from the physical information input unit 14 to derive, by calculation, the BMI as a physical parameter related to the weight of the living organism.

Furthermore, the physical parameter derivation unit 41 uses the height which is input from the physical information input unit 14 and the bioelectrical impedance acquired as bioelectric information by the first acquisition unit 20 to derive the impedance index of the living organism.

The second acquisition unit 21 in the present embodiment acquires the above-described physical parameters, yet the present invention is not limited in this way. For example, it is also possible to use a physical parameter related to muscle mass of the living organism derived indirectly using the gender or age which is input from the physical information input unit 14, or a physical parameter related to the muscle mass of the living organism by deriving the muscle mass and muscle ratio of each body part of the living organism using the electrodes of the first electrode unit 11 and the second electrode unit 17 in the first acquisition unit 20. Furthermore, the body weight acquired by the weight measurement unit 40 may be used directly as a physical parameter of the living organism. As described above, in the present embodiment, the physical parameter derivation unit 41 derives the muscle ratio using the fat mass, estimated bone mass, and the like that are calculated from the measured values of the bioelectrical impedance and body weight, yet the muscle ratio may be directly derived from the bioelectrical impedance acquired by the first acquisition unit 20, the body weight measured by the weight measurement unit 40, and the height which is input from the physical information input unit 14.

In the present embodiment, a portion of physical information such as the height, gender, age, and the like of the subject being measured is input from the physical information input unit 14. The second acquisition unit 21, however, may include a height measurement unit (not illustrated) that can measure the body height or body part length of the living organism, and the physical parameter derivation unit 41 may use the values measured by the height measurement unit to derive physical parameters.

<Calculation Unit 22>

The calculation unit 22 calculates an index in accordance with the proportion, in muscle tissue, of muscle fiber to interstitial tissue based on a physical parameter and on at least one of a first parameter represented as a ratio between the resistance component R and the reactance component X and a second parameter represented as a ratio between the first impedance $Z_{low}$ and the second impedance $Z_{high}$.

The "first parameter" is a parameter calculated from the resistance component R and the reactance component X of the bioelectrical impedance acquired by the first acquisition unit 20. The "second parameter" is a parameter calculated from the first impedance $Z_{low}$ and the second impedance $Z_{high}$ acquired by the first acquisition unit 20. The "physical parameter" is the parameter acquired by the second acquisition unit 21. As described above, in the present embodiment, the bioelectric information calculation unit 31 for the first acquisition unit 20 calculates at least one of the first parameter and the second parameter, yet alternatively the calculation unit 22 may calculate at least one of the first parameter and the second parameter.

Furthermore, the "index in accordance with the proportion, in muscle tissue, of muscle fiber to interstitial tissue" refers to the proportion, in muscle tissue, of muscle fiber to interstitial tissue (muscle quality), to a muscle quality index that is an index representing the proportion, in muscle tissue, of muscle fiber to interstitial tissue, or to a total muscle quality index that includes at least a muscle quality index as a factor. All of these are indices related to assessing muscle quality. In this context, "muscle tissue" means "a collection of muscle bundle covered by fascia", and "muscle bundle" means "tissue that is covered by perimysium and that includes muscle fibers and interstitial tissue located between the muscle fibers". Furthermore, "muscle fiber" refers to muscle cells, and "interstitial tissue" refers to all tissue other than muscle fiber within a muscle bundle.

The "total muscle quality index" includes a comprehensive index related to muscle quality taking into consideration the proportion of fast muscle and slow muscle, fat in interstitial tissue, invasion of connective tissue and the like, in addition to the muscle quality index.

As the index in accordance with the proportion, in muscle tissue, of muscle fiber to interstitial tissue, the calculation unit 22 in the present embodiment calculates the muscle quality index, which is an index representing the proportion, in muscle tissue, of muscle fiber to interstitial tissue. Specifically, the muscle quality index in the present embodiment is calculated using the contributing ratio for muscle quality and the contributing ratio for muscle mass of a variety of parameters (BMI, muscle mass, and the like) that are related to muscle strength and that are determined, using a statistical method such as principal component analysis, from experimental results obtained for numerous subjects. Note that "muscle mass" refers to the weight or volume of muscle.

As the above-described parameters related to muscle strength, the calculation unit 22 in the present embodiment uses at least one of the first parameter and the second parameter, acquired by the first acquisition unit 20, and the physical parameter acquired by the second acquisition unit 21. The calculation unit 22 in the present embodiment then calculates muscle quality points as the muscle quality index by multiplying contributing ratios a1 and a2 to aN for muscle quality of these statistically determined parameters respectively by an acquired value P1 of the parameter acquired by the first acquisition unit 20 and acquired values P2 to PN of the physical parameters acquired by the second acquisition unit 21, taking the sum of all of the terms (see Equation 3 below).

$$\text{muscle quality points} = a1 \times (P1) + a2 \times (P2) + \ldots + aN \times (PN) \quad \text{(Equation 3)}$$

Note that in the present embodiment, the acquired value P1 of the parameter acquired by the first acquisition unit 20, which is at least one of the first parameter and the second parameter, and the acquired values P2 to PN of the physical parameters acquired by the second acquisition unit 21 are used after conversion into generalized numerical values. As a method for converting a numerical value k into a generalized numerical value k', Equation 4 below may, for example, be used.

$$k' = (k - \text{average of } k)/\text{standard deviation of } k \quad \text{(Equation 4)}$$

In the present embodiment, BMI, total body muscle ratio, the muscle mass of legs within the body weight as a body part/body weight muscle ratio, and the impedance index of the living organism are used as physical parameters, yet it suffices to use at least one physical parameter, and the present invention is not limited to use of all of these physical parameters. For example, the total body muscle mass, body part muscle ratio, body part/body weight muscle ratio for a body part other than legs, and the like may be used in addition to or instead of the above physical parameters. Using a plurality of physical parameters, however, improves the accuracy of the muscle quality index as compared to when using one physical parameter.

The parameter that is at least one of the first parameter and the second parameter acquired by the first acquisition unit 20 changes in accordance with the ratio between muscle intracellular fluid and muscle extracellular fluid, yet with this parameter, it is difficult to judge muscular atrophy and muscular development when muscle intracellular fluid and muscle extracellular fluid decrease or increase by the same degree. The calculation unit 22 of the apparatus 100 for assessing muscle quality, however, calculates an index using not only at least one of the first parameter and the second parameter acquired by the first acquisition unit 20 but also at least one of the above-described physical parameters. Hence, the absolute amount of muscle mass is reflected in the calculated index. Therefore, the index also allows for judging of muscular atrophy and muscular development when muscle intracellular fluid and muscle extracellular fluid decrease or increase by the same degree (for example, when muscle fiber atrophies and the overall muscle tissue shrinks at the same time).

Examples of the physical parameter that can be used by the calculation unit 22 include a physical parameter related to muscle mass of the living organism, a physical parameter related to weight of the living organism, the impedance index of the living organism, and the like, yet use of a physical parameter related to muscle mass of the living organism is particularly preferable. Within the body, the legs are most susceptible to weakening of muscle mass, and therefore a physical parameter related to muscle mass of the legs is preferable among physical parameters related to muscle mass of the living organism.

In addition to the above-described muscle quality points, the calculation unit 22 in the present embodiment also calculates muscle mass points as the muscle mass index.

The muscle mass index is calculated using the above-described statistically determined contributing ratios for muscle mass. Specifically, the calculation unit 22 calculates muscle quality points as the muscle quality index and also uses the same parameters as the parameters used to calculate the muscle quality points in order to calculate muscle mass points as the muscle mass index by multiplying contributing ratios b1 and b2 to bN for muscle mass respectively by calculated values P1 and P2 to PN of the parameters, taking the sum of all of the terms (see Equation 5 below).

$$\text{muscle mass points} = b1 \times (P1) + b2 \times (P2) + \ldots + bN \times (PN) \quad \text{(Equation 5)}$$

For the parameter acquired by the first acquisition unit 20, which is at least one of the first parameter and the second parameter, the contributing ratio a1 for muscle quality is substantially large, whereas the contributing ratio b1 for muscle mass is smaller than the contributing ratio a1 for muscle quality. With regard to the body part/body weight muscle ratio and the impedance index of the living organism as physical parameters acquired by the second acquisition unit 21, when P2 in Equation 5 above is the body part/body weight muscle ratio and P3 is the impedance index of the living organism, the contributing ratios a2 and a3 for muscle quality are small, whereas the contributing ratios b2 and b3 for muscle mass are larger than the contributing ratios a2 and a3 for muscle quality.

In general, muscle strength can be assessed for younger people by assessing muscle mass. In the case of older people, however, muscle fiber among muscle tissue becomes thinner and is progressively replaced by fat or connective tissue. Therefore, muscle strength cannot be assessed accurately by merely assessing muscle mass, which is the actual size of muscle tissue. In the present embodiment, however, muscle is assessed with both the muscle mass index and the muscle quality index, and hence the factors constituting muscle strength can be assessed from these two indices.

<Control Unit 23>

The control unit 23 is connected to the first acquisition unit 20, second acquisition unit 21, calculation unit 22, output unit 15, and storage unit 26 and controls each of these units.

<Output Unit 15>

The output unit 15 in the present embodiment includes the display unit 16. The display unit 16 displays information in accordance with a calculated value of the muscle quality index and a calculated value of the muscle mass index calculated by the calculation unit 22.

Figure 6:
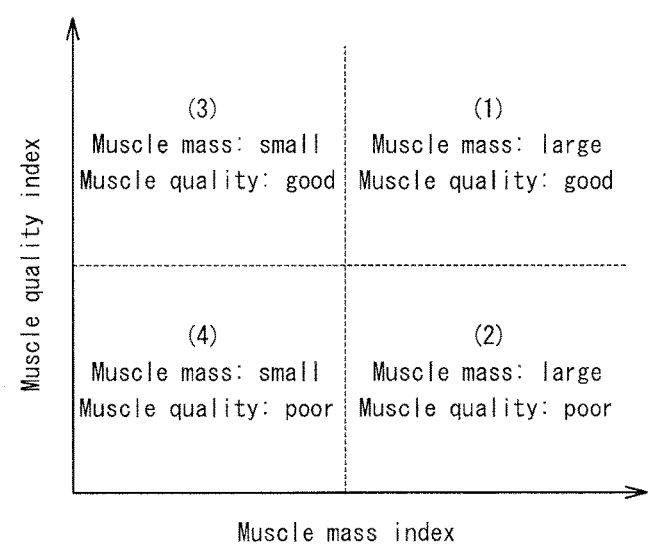
FIG. 6 illustrates muscle strength assessment using a muscle mass index and a muscle quality index.

Examples of the information in accordance with the calculated value of the muscle quality index and the calculated value of the muscle mass index include the current muscle state, advice, and a proposed training plan that take into consideration the muscle mass and quality. FIG. 6 is a graph with the muscle mass index on the horizontal axis and the muscle quality index on the vertical axis. In region (1), muscle mass is large, and muscle quality is good. In region (2), muscle mass is large, yet muscle quality is poor. In region (3), muscle mass is small, yet muscle quality is good. In region (4), muscle mass is small, and muscle quality is also poor.

In the present embodiment, predetermined thresholds are set in advance for the muscle quality points as the muscle quality index and for the muscle mass points as the muscle mass index. Accordingly, after being calculated, the muscle quality points and the muscle mass points of the subject being measured are compared with the thresholds to determine which of the regions (1) to (4) the determination result belongs to, and corresponding information is output to the display unit 16.

When, for example, the determination result belongs to region (1), the information in accordance with the determination result is the message "you should maintain your lifestyle". By seeing this message, subjects being measured can see that they have a good lifestyle and may be motivated to maintain their lifestyle.

When the determination result belongs to region (2), the message "you have muscle mass, but the quality is poor. You should do resistance training", for example, is displayed on the display unit 16. By seeing this message, subjects being measured can learn about their muscle quality, which is difficult to judge by appearances, and may be prompted to rethink their lifestyle. Note that the type of muscle belonging to region (2) is relatively frequent among people who exercised when they were young but no longer exercise now. Therefore, resistance training may be suggested in order first to train fast muscle, which atrophies before slow muscle.

When the determination result belongs to region (3), the message "you have small muscle mass, but the quality is good. You should do resistance training and endurance training", for example, is displayed on the display unit 16. By seeing this message, subjects being measured can learn that their muscle quality is good and may be prompted to improve their lifestyle. Note that the type of muscle belonging to region (3) is relatively frequent among people who have hardly exercised throughout their life. Therefore, both resistance training and endurance training may be suggested as a training plan.

When the determination result belongs to region (4), the message "you should greatly improve your lifestyle", for example, is displayed on the display unit 16. By seeing this message, subjects being measured can learn about the state of their muscles and may be prompted to improve their lifestyle. This message may also prompt subjects to be careful about falls or the like in their day-to-day life.

In the present embodiment, the current muscle state, advice, proposed training plan, and the like are used as information in accordance with the calculated value of the muscle quality index and the calculated value of the muscle mass index, yet the information is not limited to these examples. The actual calculated values, for example, may be displayed on the display unit 16. A graph showing a plot of the calculated value of the muscle quality index and the calculated value of the muscle mass index may also be displayed on the display unit 16.

In the present embodiment, the predetermined threshold for the muscle quality points as the muscle quality index and the predetermined threshold for the muscle mass points as the muscle mass index are set using the average values of the muscle mass points and muscle quality points obtained from a group of healthy individuals, a group of people identified by a doctor, nurse, or the like as being at risk of requiring nursing care in the future (referred to below as "older people at risk of requiring nursing care"), and a group of people identified by a doctor, nurse, or the like as requiring nursing care (referred to below as "older people requiring nursing care"). Specifically, for the muscle mass points and for the muscle quality points, the average of the average values for the above three groups is set as the threshold.

In addition to the above-described method for setting the thresholds, it is possible to use a method for setting the thresholds based on the standard deviation, for any two groups, with respect to the averages of the muscle mass points and the muscle quality points obtained for the three groups, i.e. healthy individuals, older people at risk of requiring nursing care, and older people requiring nursing care. For example, using the two groups G1 and G2 among these three groups, the thresholds for G1 and G2 can be set based on a coefficient, s, satisfying Equation 6 below and on the standard deviations.

$$\text{(average of } G1) - s \times \text{(standard deviation of } G1) = \text{(average of } G2) + s \times \text{(standard deviation of } G2) \quad \text{(Equation 6)}$$

Furthermore, the method for setting the thresholds is not limited to the above-described methods and may be any of a variety of methods, such as a method for setting the thresholds based on a clearly defined numerical value, such as the sarcopenia index, or a method for setting the thresholds taking the subject's age into consideration.

<Storage Unit 26>

The storage unit 26 includes a Random Access Memory (RAM) 42 and a Read Only Memory (ROM) 43. The RAM 42 temporarily stores information related to the body such as gender, height, age, and the like which is input from the physical information input unit 14, measured data, calculation results, and the like. The ROM 43 stores a control program for the entire apparatus 100 for assessing muscle quality, a control program for the control unit 30 of the first acquisition unit 20, calculation formulas set in advance for the muscle quality index and muscle mass index, a program for determining the muscle quality index and the muscle mass index, the alternating current frequencies supplied to the first electrode unit 11 and the second electrode unit 17 in the first acquisition unit 20, and the like.

So far, the structure of the apparatus 100 for assessing muscle quality has mainly been described. The following illustrates actual results for the muscle quality index and the muscle mass index calculated by the apparatus 100 for assessing muscle quality with the above-described method.

\<Results for Muscle Mass Points and Muscle Quality Points Calculated by the Apparatus 100 for Assessing Muscle Quality>

Figure 7:
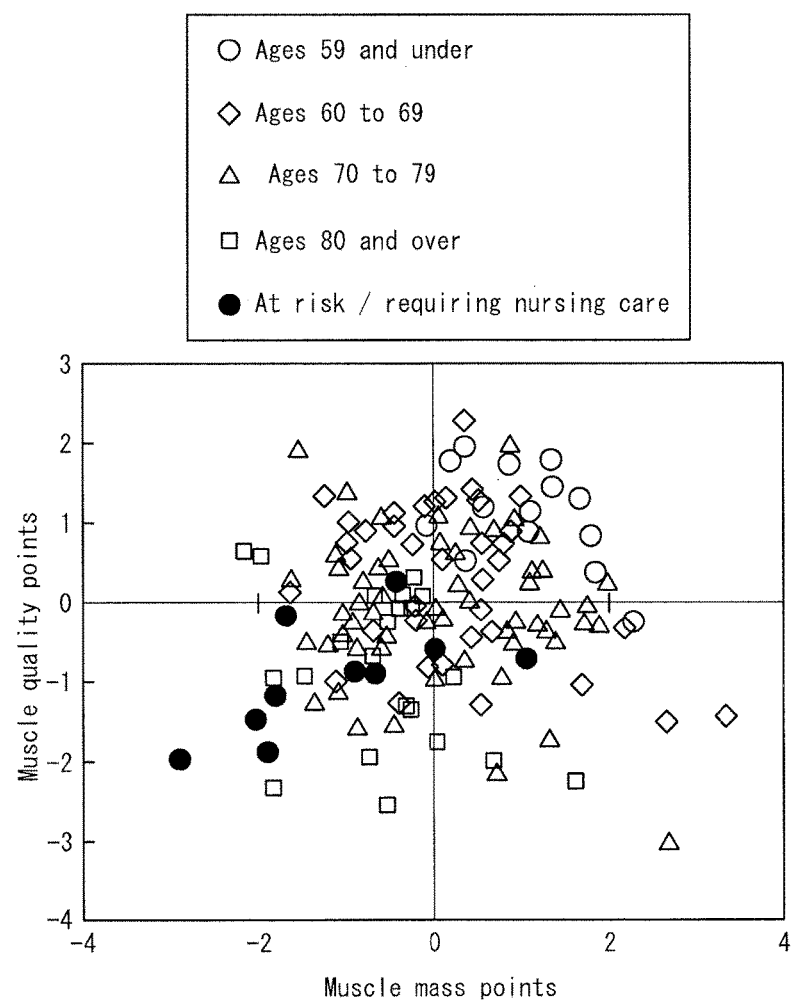
FIG. 7 is a graph of a data distribution of muscle mass points and muscle quality points calculated for subjects.

FIG. 7 is a graph of an actual data distribution for healthy male individuals, older males at risk of requiring nursing care, and older males requiring nursing care, with the muscle mass points on the horizontal axis and the muscle quality points on the vertical axis. Note that in FIG. 7, the data for healthy individuals is divided into age ranges. Specifically, as illustrated in the legend for FIG. 7, the healthy individuals are divided into four age ranges: 59 and under, 60 to 69, 70 to 79, and 80 and over.

FIG. 7 shows how the muscle quality points calculated by the apparatus 100 for assessing muscle quality in the present embodiment decrease with age, i.e. muscle quality tends to worsen with age. It is also clear that the muscle quality points for older people at risk of requiring nursing care and older people requiring nursing care tend to be lower than for healthy individuals. The muscle quality points calculated as the muscle quality index by the apparatus 100 for assessing muscle quality in the present embodiment thus successfully illustrate the worsening of muscle quality with age.

Furthermore, FIG. 7 shows how not only muscle quality but also muscle mass tends to decrease with age. In other words, it is clear that with age, the data distribution shifts from the upper right towards the lower left. It is also clear that like the muscle quality points, the muscle mass points for older people at risk of requiring nursing care and older people requiring nursing care tend to be lower than for healthy individuals. Note that the horizontal axis indicating 0 muscle quality points in FIG. 7 indicates the average of the muscle quality points for all subjects, and the vertical axis indicating zero muscle mass points in FIG. 7 indicates the average of the muscle mass points for all subjects. In FIG. 7, these vertical and horizontal axes are shown, yet additionally including reference axes showing the average by age range makes the above tendencies with age even clearer.

Figure 8:
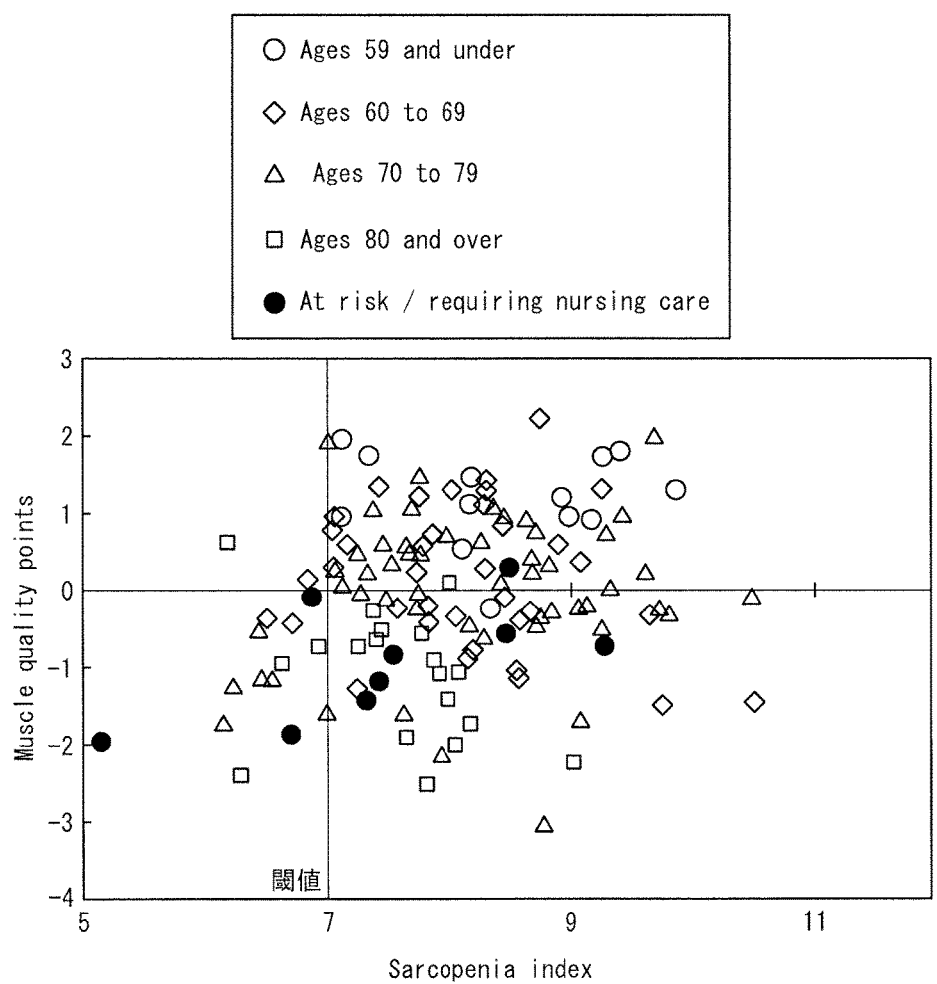
FIG. 8 is a graph of a data distribution of a sarcopenia index and muscle quality points calculated for subjects.

FIG. 8 is a graph of an actual data distribution for healthy male individuals, older males at risk of requiring nursing care, and older males requiring nursing care, with the sarcopenia index on the horizontal axis and the muscle quality points on the vertical axis. The sarcopenia index is an index calculated as limb muscle mass/height$^2$ and is generally used as an index of muscle weakness. Similar tendencies as in FIG. 7 can be read from FIG. 8 as well.

As described above, the muscle quality index calculated by the apparatus 100 for assessing muscle quality successfully illustrates the worsening of muscle quality with age. The muscle mass index also successfully illustrates the well-known reduction in muscle mass with age. Accordingly, it is clear that the muscle quality index and muscle mass index in the present embodiment are valid indices for assessing muscle quality and muscle mass.

In the present embodiment, a body composition meter 100a including the platform unit 1 and the grip unit 2 has been described as the apparatus 100 for assessing muscle quality. It suffices, however, for the apparatus 100 for assessing muscle quality to include the first acquisition unit 20 that acquires bioelectric information including at least one of (i) the resistance component R and the reactance component X of bioelectrical impedance and (ii) the first impedance $Z_{low}$ measured by supplying alternating current at a predetermined low frequency (for example, 5 kHz) to a living organism and the second impedance $Z_{high}$ measured by supplying alternating current at a predetermined high frequency (for example, 250 kHz) to the living organism, the second acquisition unit 21 that acquires a physical parameter related to physique of the living organism, and the calculation unit 22 that calculates an index in accordance with the proportion, in muscle tissue, of muscle fiber to interstitial tissue based on a physical parameter and on at least one of a first parameter represented as the ratio between the resistance component R and the reactance component X and a second parameter represented as a ratio between the first impedance $Z_{low}$ and the second impedance $Z_{high}$. The specific configurations of these units are not limited to the configurations illustrated in the present embodiment. For example, the apparatus 100 for assessing muscle quality may include either the platform unit 1 or the grip unit 2. Furthermore, the configuration of the electrodes is not limited to that illustrated in the present embodiment. For example, deformable electrodes such as attachable electrodes may be adopted to allow for use for bedridden elderly people or the like.

The first acquisition unit 20 in the present embodiment includes a unit that measures bioelectric information, yet the first acquisition unit 20 may include a bioelectric information input unit that allows for external input of at least one of (i) the resistance component R and the reactance component X and (ii) the first impedance $Z_{low}$ and the second impedance $Z_{high}$ and may acquire the bioelectric information from the bioelectric information input unit. Note that the bioelectric information input unit may be configured to allow for external input of at least one of the first parameter represented as the ratio between the resistance component R and the reactance component X and the second parameter represented as the ratio between the first impedance $Z_{low}$ and the second impedance $Z_{high}$.

Figure 9:
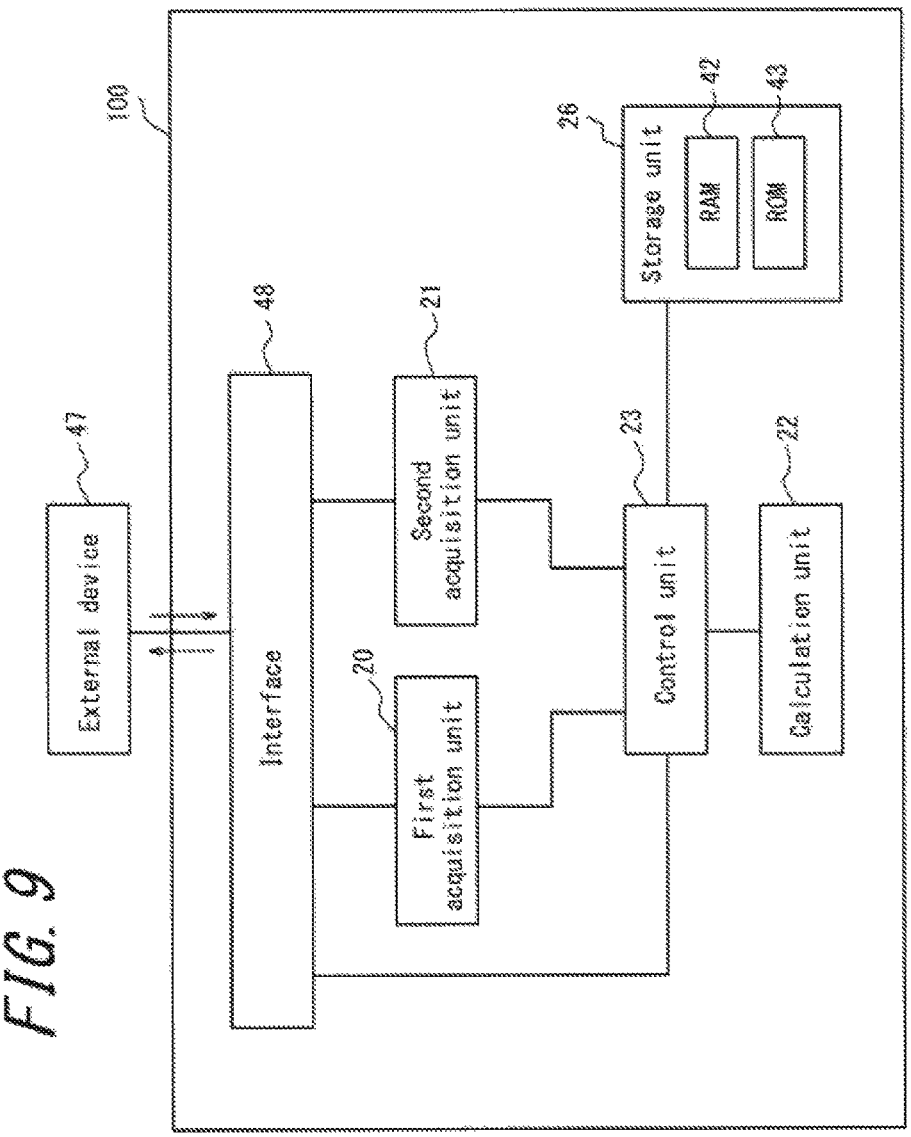
FIG. 9 is a block diagram illustrating a modification to the apparatus 100 for assessing muscle quality.

Furthermore, as illustrated in FIG. 9, the apparatus 100 for assessing muscle quality may include a bioelectric information reception unit (interface 48) that allows the first acquisition unit 20 to receive at least one of (i) the resistance component R and the reactance component X and (ii) the first impedance $Z_{low}$ and the second impedance $Z_{high}$ from an external device 47, such as a desktop computer, a laptop computer, a smart phone, a tablet PC, or the like, by wired or wireless communication. In other words, the first acquisition unit 20 may receive at least one of the first parameter and the second parameter from the external device 47 via the bioelectric information reception unit. Note that the bioelectric information reception unit may be configured to receive at least one of the first parameter represented as the ratio between the resistance component R and the reactance component X and the second parameter represented as the ratio between the first impedance $Z_{low}$ and the second impedance $Z_{high}$ from the external device 47.

In the present embodiment, the second acquisition unit 21 includes the body weight measurement unit 40a as the weight measurement unit 40 that can measure the weight of the living organism and includes the physical information input unit 14 that allows for input of information related to the body and derives the physical parameter from the value measured by the weight measurement unit 40 and the information related to the body which is input from the physical information input unit 14. Instead of including the weight measurement unit 40 that measures the weight of the living organism, however, the body weight of the living organism and the weight of each body part of the living organism may also be input from the physical information input unit 14.

Furthermore, a configuration may be adopted whereby the apparatus 100 for assessing muscle quality includes a physical information reception unit (interface) that allows the second acquisition unit 21 to receive information related to the body for deriving the physical parameter from an external device 47, such as a computer, by wired or wireless communication, and based on the physical information received by the physical information reception unit, the physical parameter derivation unit 41 may derive the physical parameter. As illustrated in FIG. 9, the apparatus 100 for assessing muscle quality may include a physical parameter reception unit (interface 48) that allows the second acquisition unit 21 to receive the actual physical parameter from the external device 47 by wired or wireless communication. In other words, a configuration may be adopted whereby the second acquisition unit 21 receives the physical parameter from the external device 47 via the physical parameter reception unit.

Additionally, the second acquisition unit 21 may include a physical parameter input unit that allows for external input of the actual physical parameter for the living organism, and the second acquisition unit 21 may acquire the physical parameter by the physical parameter being input from the physical parameter input unit.

As described above, in various ways, the first acquisition unit 20 can not only acquire at least one of (i) the resistance component R and the reactance component X and (ii) the first impedance $Z_{low}$ and the second impedance $Z_{high}$, but can also acquire at least one of the first parameter represented as the ratio between the resistance component R and the reactance component X and the second parameter represented as the ratio between the first impedance $Z_{low}$ and the second impedance $Z_{high}$. In various ways, the second acquisition unit 21 can also acquire the physical parameter and information related to the body for deriving the physical parameter.

In the present embodiment, the output unit 15 includes the display unit 16 that outputs the muscle quality index calculated by the calculation unit 22. As illustrated in FIG. 9, however, the output unit 15 may include a data transmission unit (interface 48) that, based on an instruction from the control unit 23, transmits the muscle quality index calculated by the calculation unit 22 to an external device 47 such as a desktop computer, laptop computer, smart phone, tablet PC, or the like that includes a display unit such as a monitor. In other words, the control unit 23 may transmit the index calculated by the calculation unit 22 to the external device 47 via the data transmission unit. The data transmission unit may be configured to transmit not only the value of the muscle quality index calculated by the calculation unit 22 but also the calculated value of the muscle mass index. The data transmission unit may also transmit information in accordance with the calculated value of the muscle quality index and the calculated value of the muscle mass index, such as a message or advice, and cause the information to be displayed on the display unit of the external device 47.

INDUSTRIAL APPLICABILITY

The present invention relates to an apparatus for assessing muscle quality and in particular to an apparatus for assessing muscle quality that can calculate an index in accordance with the proportion of muscle fiber in muscle tissue.

REFERENCE SIGNS LIST

1: Platform unit
2: Grip unit
11: First electrode unit
12: First current supply electrodes (collectively)
12a, 12b: First current supply electrodes (individually)
13: First voltage measurement electrodes (collectively)
13a, 13b: First voltage measurement electrodes (individually)
14: Physical information input unit
14a: Setting key
14b: Up key
14c: Down key
15: Output unit
16: Display unit
17: Second electrode unit
18: Second current supply electrodes (collectively)
18a, 18b: Second current supply electrodes (individually)
19: Second voltage measurement electrodes (collectively)
19a, 19b: Second voltage measurement electrodes (individually)
20: First acquisition unit
21: Second acquisition unit
22: Calculation unit
23: Control unit
26: Storage unit
27: First current generation unit
28: First voltage measurement unit
29: First analog/digital converter
30: Control unit for first acquisition unit
31: Bioelectric information calculation unit for first acquisition unit
32: Second current generation unit
33: Second voltage measurement unit
34: Second analog/digital converter
37: First reference current detection unit
38: First alternating current generation unit
39: First frequency setting unit
40: Weight measurement unit
40a: Body weight measurement unit
41: Physical parameter derivation unit
42: RAM
43: ROM
44: Second reference current detection unit
45: Second alternating current generation unit
46: Second frequency setting unit
47: External device
48: Interface
100: Apparatus for assessing muscle quality
200: Cable

The invention claimed is:

1. An apparatus for assessing muscle quality, the apparatus comprising:
a first electrode;
a second electrode;
a platform configured to receive a living organism thereon; and
at least one hardware processor configured to implement:
controlling at least the first electrode to output an alternating current at different frequencies to the living organism,
acquiring, from the living organism and by at least the second electrode, bioelectric information comprising first impedance measured by supplying the alternating current at a predetermined low frequency to the living organism and second impedance measured by supplying the alternating current at a predetermined high frequency to the living organism, the different frequencies comprising the predetermined low frequency and the predetermined high frequency;
acquiring a physical parameter related to a physique of the living organism;

calculating not only a muscle quality index indicating a proportion, in muscle tissue, of muscle fiber to interstitial tissue, but also a muscle mass index indicating a weight or value of muscle based on acquired parameters comprising the physical parameter and a second parameter represented as a ratio between the first impedance and the second impedance; and providing a graph indicating a relationship between the muscle quality index and the muscle mass index of the living organism, wherein the physical parameter comprises a parameter related to muscle mass of the living organism, and wherein the muscle quality index is calculated by multiplying muscle quality contributing ratios of the acquired parameters respectively by values of the acquired parameters, and by calculating a sum of values of the acquired parameters multiplied by the muscle quality contributing ratios of the acquired parameters respectively, wherein at least one of the first electrode and the second electrode are included in the platform, and wherein the at least one hardware processor is further configured to control acquiring the bioelectric information from the living organism, while the living organism stands on the platform.

2. The apparatus of claim 1, wherein
the physical parameter further comprises a parameter related to muscle mass of legs of the living organism.

3. The apparatus of claim 1, wherein the physical parameter further comprises a parameter related to a weight of the living organism.

4. The apparatus of claim 1, wherein the physical parameter further comprises an impedance index of the living organism which is a height squared divided by an absolute value of bioelectrical impedance, the height indicating a body height or a body part length of the living organism.

5. The apparatus of claim 1, wherein the at least one hardware processor is further configured to implement:
calculating a muscle mass index by multiplying muscle mass contributing ratios of the acquired parameters respectively by the values of the acquired parameters, and by calculating the sum of the values of the acquired parameters multiplied by the muscle mass contributing ratios of the acquired parameters respectively.

6. The apparatus of claim 5, wherein the at least one hardware processor is further configured to implement:
controlling a display unit to display a calculated value of the muscle quality index and a calculated value of the muscle mass index, or information based on the calculated value of the muscle quality index and on the calculated value of the muscle mass index.

7. The apparatus of claim 1, wherein the at least one hardware processor is further configured to implement:
controlling an interface to exchange information with an external device.

8. The apparatus of claim 7, wherein
the second parameter is received from the external device via the interface, and
the physical parameter is received from the external device via the interface.

9. The apparatus of claim 8, the at least one hardware processor is further configured to implement:
transmitting the calculated muscle quality index to the external device via the interface.

10. The apparatus of claim 7, wherein the at least one hardware processor is further configured to implement:

transmitting the calculated muscle quality index to the external device via the interface.

11. The apparatus according to claim 1, wherein the graph provides a description of muscle mass and muscle quality and a message indicating a type of training to perform.

12. The apparatus according to claim 1,
wherein the second parameter indicates the ratio between the first impedance and the second impedance.

13. An apparatus for assessing muscle quality, the apparatus comprising:
a first electrode;
a second electrode;
a platform configured to receive a living organism thereon;
a grip unit connected to the platform by a cable; and
at least one hardware processor configured to implement:
controlling at least the first electrode to output an alternating current at different frequencies to the living organism;
acquiring, from the living organism and by at least the second electrode, bioelectric information comprising at least one of (i) a resistance component and a reactance component of bioelectrical impedance and (ii) first impedance measured by supplying the alternating current at a predetermined low frequency to a living organism and second impedance measured by supplying the alternating current at a predetermined high frequency to the living organism, the different frequencies comprising the predetermined low frequency and the predetermined high frequency;
acquiring a physical parameter related to a physique of the living organisms;
calculating not only a muscle quality index indicating a proportion, in muscle tissue, of muscle fiber to interstitial tissue, but also a muscle mass index indicating a weight or volume of muscle, based on acquired parameters comprising the physical parameter and at least one of a first parameter represented as a ratio between the resistance component and the reactance component and a second parameter represented as a ratio between the first impedance and the second impedance; and
providing a graph indicating a relationship between the muscle quality index and the muscle mass index of the living organism, wherein
the physical parameter comprises a parameter related to muscle mass of the living organism, and wherein
the muscle quality index is calculated by multiplying muscle quality contributing ratios of the acquired parameters respectively by values of the acquired parameters, and by calculating a sum of values of the acquired parameters multiplied by the muscle quality contributing ratios of the acquired parameters respectively,
wherein at least one of the first electrode and the second electrode are included in the platform,
wherein another one of the first electrode and the second electrode is included in the grip unit, and
wherein the at least one hardware processor is further configured to control outputting of the alternating current at different frequencies to the living organism, and acquiring the bioelectric information from the living organism, while the living organism stands on the platform and grips the grip unit.

14. An apparatus for assessing muscle quality, the apparatus comprising:
a first electrode;
a second electrode;
a platform configured to receive a living organism thereon; and
at least one hardware processor configured to implement:
controlling at least the first electrode to output an alternating current to the living organism,
acquiring, from the living organism and by at least the second electrode, bioelectric information comprising a resistance component and a reactance component of bioelectrical impedance;
acquiring a physical parameter related to a physique of the living organism;
calculating not only a muscle quality index indicating a proportion, in muscle tissue, of muscle fiber to interstitial tissue, but also a muscle mass index indicating a weight or value of muscle based on acquired parameters comprising the physical parameter and a first parameter represented as a ratio between the resistance component and the reactance component; and
providing a graph indicating a relationship between the muscle quality index and the muscle mass index of the living organism, wherein
the physical parameter comprises a parameter related to muscle mass of the living organism, and wherein
the muscle quality index is calculated by multiplying muscle quality contributing ratios of the acquired parameters respectively by values of the acquired parameters, and by calculating a sum of values of the acquired parameters multiplied by the muscle quality contributing ratios of the acquired parameters respectively,
wherein at least one of the first electrode and the second electrode are included in the platform, and
wherein the at least one hardware processor is further configured to control acquiring the bioelectric information from the living organism, while the living organism stands on the platform.

15. The apparatus of claim 14, wherein
the physical parameter further comprises a parameter related to muscle mass of legs of the living organism.

16. The apparatus of claim 14, wherein the physical parameter further comprises a parameter related to a weight of the living organism.

17. The apparatus of claim 14, wherein the physical parameter further comprises an impedance index of the living organism which is a height squared divided by an absolute value of bioelectrical impedance, the height indicating a body height or a body part length of the living organism.

18. The apparatus of claim 14, wherein the at least one hardware processor is further configured to implement:
calculating a muscle mass index by multiplying muscle mass contributing ratios of the acquired parameters respectively by the values of the acquired parameters, and by calculating the sum of the values of the acquired parameters multiplied by the muscle mass contributing ratios of the acquired parameters respectively.

19. The apparatus of claim 14, wherein the at least one hardware processor is further configured to implement:
controlling an interface to exchange information with an electrical device.

20. The apparatus according to claim 14, wherein the graph provides a description of muscle mass and muscle quality and a message indicating a type of training to perform.

* * * * *